(12) United States Patent
van Damme et al.

(10) Patent No.: US 6,864,102 B2
(45) Date of Patent: Mar. 8, 2005

(54) DEVICE FOR PERFORMING AN ASSAY, A METHOD FOR MANUFACTURING SAID DEVICE, AND USE OF A MEMBRANE IN THE MANUFACTURE OF SAID DEVICE

(75) Inventors: Hendrik Sibolt van Damme, Hertogenbosch (NL); Hermanus Johannes Maria Kreuwel, Schijndel (NL)

(73) Assignee: PamGene International B.V., 's-Hertogenbosch (NL)

( * ) Notice: Subject to any disclaimer, the term of this patent is extended or adjusted under 35 U.S.C. 154(b) by 428 days.

(21) Appl. No.: 09/845,198

(22) Filed: May 1, 2001

(65) Prior Publication Data

US 2002/0127738 A1 Sep. 12, 2002

Related U.S. Application Data

(63) Continuation of application No. 09/403,559, filed as application No. PCT/EP98/04938 on Jul. 7, 1998, now Pat. No. 6,225,131.

(30) Foreign Application Priority Data

Jul. 11, 1997 (EP) ............................................. 97202140

(51) Int. Cl.$^7$ ........................................... G01N 33/543
(52) U.S. Cl. .......................... 436/518; 422/57; 422/58; 435/5; 435/6; 435/7.1; 435/287.1; 435/287.2; 435/810; 436/524; 436/525
(58) Field of Search ......................... 422/57, 58; 435/5, 435/6, 7.1, 287.1, 287.2, 810; 436/518, 524, 525

(56) References Cited

U.S. PATENT DOCUMENTS

| | | |
|---|---|---|
| 3,652,761 A | 3/1972 | Weetall |
| 3,671,410 A | 6/1972 | Stahr ........................... 204/56 |
| 4,427,415 A | 1/1984 | Cleveland |
| 4,693,985 A | 9/1987 | Degen et al. ................ 436/531 |
| 4,777,021 A | 10/1988 | Wertz et al. |
| 5,772,735 A | 6/1998 | Sehgal et al. ................... 95/45 |
| 5,843,767 A | 12/1998 | Beattie ..................... 435/287.1 |
| 6,225,131 B1 * | 5/2001 | van Damme et al. ........ 436/524 |
| 6,635,493 B2 * | 10/2003 | van Damme et al. ........ 436/524 |

FOREIGN PATENT DOCUMENTS

| | | |
|---|---|---|
| EP | 0 178 831 B1 | 7/1991 |
| GB | 1 432 713 A | 4/1976 |
| WO | WO 95/11755 | 5/1995 |
| WO | WO 99/02266 | 1/1999 |

OTHER PUBLICATIONS

Rigby et al., "An Anodizing Process for the Production of Inorganic Microfiltration Membranes," Trans. Inst. Metal Finish, 1990, vol. 68, (3), pp. 95–98.
Socransky et al. (1994). "Checkerboard" DNA–DNA hybridization. BioTechniques. 17(4):788–792.
Alderton et al. (1994). Automated DNA hybridization. Anal. Biochem. 218:98–102.
Tonucci et al. (1992). Nanochannel array glass. Science. 258:783–785.
Rigby et al., Trans. Inst. Metal Finish., 68(3):95–98 (1990).
Fadda et al., Biotechnology and Applied Biochem., 16:221–227, 1992.

* cited by examiner

Primary Examiner—Christopher L. Chin
(74) Attorney, Agent, or Firm—Amster, Rothstein & Ebenstein LLP

(57) ABSTRACT

The present invention relates to a device for performing an assay, which device comprises a substrate having oriented through-going channels, said channels opening out on a surface for sample application, the channels in at least one area of the surface for sample application being provided with a first binding substance capable of binding to an analyte. The object of the present invention is to provide a substrate having both a high channel density and a high porosity, allowing high density arrays comprising different first binding substances to be applied to the surface for sample application. More in particular, the object of the present invention is to provide a device comprising a relatively cheap substrate that does not require the use of any typical microfabrication technology and, that offers an improved control over the liquid distribution over the surface of the substrate. The above objects are achieved with a device as mentioned above wherein the porous substrate is an electrochemically manufactured metal oxide membrane.

20 Claims, No Drawings

SEQUENCE LISTING

```
<160> NUMBER OF SEQ ID NOS: 5

<210> SEQ ID NO 1
<211> LENGTH: 145
<212> TYPE: RNA
<213> ORGANISM: Human immunodeficiency virus type 1

<400> SEQUENCE: 1
cccugcuaug ucacuucccc uugguucucu caucuggccu ggugcaauag gcccugcaug     60
cacuggaugc acucuauccc auucugcagc uuccucauug auggucucuu uuaacauuug    120
cauggcugcu ugauguccccc ccacu                                          145

<210> SEQ ID NO 2
<211> LENGTH: 145
<212> TYPE: RNA
<213> ORGANISM: Human immunodeficiency virus type 1

<400> SEQUENCE: 2
cccugcuaug ucacuucccc uugguucucu caucuggccu ggugcaauag gcccugcaug     60
cgacugucau cuaucuacac ugucugcagc uuccucauug auggucucuu uuaacauuug    120
cauggcugcu ugaugucccc ccacu                                          145

<210> SEQ ID NO 3
<211> LENGTH: 24
<212> TYPE: DNA
<213> ORGANISM: Human immunodeficiency virus type 1
```

```
<400> SEQUENCE: 3
gaatgggata gagtgcatcc agtg                                          24

<210> SEQ ID NO 4
<211> LENGTH: 24
<212> TYPE: DNA
<213> ORGANISM: Human immunodeficiency virus type 1

<400> SEQUENCE: 4
gacagtgtag atagatgaca gtcg                                          24

<210> SEQ ID NO 5
<211> LENGTH: 25
<212> TYPE: DNA
<213> ORGANISM: Human immunodeficiency virus type 1

<400> SEQUENCE: 5
tgttaaaaga gaccatcaat gagga                                         25
```

DEVICE FOR PERFORMING AN ASSAY, A METHOD FOR MANUFACTURING SAID DEVICE, AND USE OF A MEMBRANE IN THE MANUFACTURE OF SAID DEVICE

CROSS-REFERENCES TO RELATED APPLICATIONS

This application is a continuation of U.S. Application Ser. No. 09/403,559 filed on Oct. 25, 1999 now U.S. Pat. No. 6,225,131 B1, which was the National Stage under 35 U.S.C. 371 of PCT/EP98/04938, filed Jul. 7, 1998, and which also claims priority to European Patent Application 97202140.6, filed Jul. 11, 1997.

The present invention relates to a device for performing an assay, which device comprises a substrate having oriented through-going channels, said channels opening out on a surface for sample application, the channels in at least one area of the surface for sample application being provided with a first binding substance capable of binding to an analyte.

Such a device is disclosed in WO95/11755 for "sequencing by hybridisation" applications. The device comprises a substrate provided with channels, the channels being oriented substantially perpendicular to the surface of the substrate. Three types of substrate are disclosed. The first type is comprised of a multitude of hollow glass fibres. It is manufactured by stacking glass fibres having an etchable core, providing the stack with flat ends, polishing those ends, and etching the cores, usually with acid. The second type of substrate is produced by electrochemical etching of a crystalline silicon wafer. First, the position of the channels as well as their size are defined using standard photolithographic methods. Subsequently the oriented channels are formed electrochemically. The third type of substrate is produced by nuclear track etching of an inorganic substrate. This method, comprising the steps of exposing the substrate to heavy, energetic charged particles and wet-etching, results in a substrate with channels scattered randomly over the surface of the substrate. With higher pore densities and porosity there is more chance of fusion of channels, which show reduced flow resistance with respect to other, non-fused channels.

All three types of substrates are quite expensive because of the labour-intensive manufacturing processes and/or expensive starting materials and wasteful operations, such as sawing and polishing, and/or expensive equipment. In addition, the substrates are characterised by a relatively low porosity of 30% and more. More advantageous, higher porosities of up to 80% are said to be achievable, but only at relatively low channel densities, with the disadvantage that the effective surface area of the channels of a particular area of the substrate is lower in comparison with a substrate having a comparable porosity but with higher channel densities (and consequently narrower channels). A further disadvantage of the silicon-based substrates as disclosed in WO 95/11755 is that they are not transparent for light. These substrates therefore prohibit the advantageous use of optical marker systems for the detection of analyte bound in the substrate. Popular optical marker systems are for instance based on enzymatically induced colour reactions, on bio- or chemiluminescence, or on photoluminescence. In the latter case both the excitation light and emitted luminescent light have to pass through the substrate material.

The object of the present invention is to overcome the above disadvantages and provide a substrate having both a high channel density and a high porosity, allowing even higher density arrays comprising different first binding substances per unit of the surface for sample application. In addition, the substrate is highly transparent for visible light. More in particular, the object of the present invention is to provide a device comprising a relatively cheap substrate that does not require the use of any typical microfabrication technology and, that offers an improved control over the liquid distribution over the surface of the substrate.

The above objects are achieved with a device wherein the porous substrate is an electrochemically manufactured metal oxide membrane.

Metal oxide membranes having through-going, oriented channels can be manufactured cheaply through electrochemical etching of a metal sheet. Metals considered are, among others, tantalum, titanium, and aluminium, as well as alloys of two or more metals and doped metals and alloys. The metal oxide membranes are transparent, especially if wet, which allows for assays using various optical techniques. Such membranes have oriented channels with well controlled diameter and advantageous chemical surface properties.

The invention thus provides a device for performing an assay, which device comprises a substrate having oriented through-going channels, said channels opening out on a surface for sample application, the channels in at least one area of the surface for sample application being provided with a first binding substance capable of binding to an analyte, wherein the substrate is an electrochemically manufactured metal oxide membrane.

According to a preferred embodiment, the first binding substance is chosen from the group consisting of a nucleic acid probe, an antibody, an antigen, a receptor, a hapten, and a ligand for a receptor.

Assays in which the device according to the present invention can be used may include sequencing by hybridisation, immunoassays, receptor/ligand assays and the like.

When the device is used as a tool to obtain DNA sequence information, a large array of areas is provided, each area comprising as a first binding substance an oligonucleotide probe of a different base-pair sequence. If a sample containing DNA or RNA fragments with a (partly) unknown sequence is brought into contact with the substrate a specific hybridisation pattern may occur, from which pattern the sequence information of the DNA/RNA can be derived. Such "sequencing by hybridisation" methods are well known in the art (see e.g. Fodor, S. P. A. et al. (1992), Science 251, 767–773 and Southern, E. M. et al. (1994) Nucleic Acids Res. 22, 1368–1373).

The device according to the present invention may also be used to screen a biological specimen, such as blood, for a large number of analytes. The array may consist of areas comprising oligonucleotide probes specific for, for example, *E. coli, S. aureus, S. pneumoniae* etc. A biological sample can be prepared as described in EP 0.389.063. If this sample is brought into contact with the substrate, the resulting hybridisation pattern can be read e.g. using a CCD camera in combination with an appropriate optical marker.

Apart from screening for bacteria, the device is suitable for the detection of viruses, as well as the classification of different subtypes of, for example, HIV- and HCV viruses, etc. Virus classification may be essential to determine potential drug resistance. In general it requires the ability to detect single point mutations in the virus RNA.

The device is also suited for performing sandwich immunoassays. In that case, it is preferred that a second antibody is used for binding to bound analyte, said second antibody for each of the analyte being recognised by a third labelled antibody. This may be achieved if the second and third antibodies are derived from different species and the third antibody is raised against antibodies of the other species. Thus it is avoided to label the second antibody for each particular analyte.

The device is also suited for performing "pepscans" as disclosed in Geysen et al., Proc. Natl. Acad. Sci. USA 81:3998–4002 (1984). In that case the first binding substances that are attached to the different areas of the substrate constitute different sequences of aminoacids. If the substrate is brought into contact with a liquid that contains a particular analyte, a reaction pattern may occur representing the specific affinity of the analyte for the different aminoacid sequences.

It is preferred that the first binding substance is covalently bound to the substrate. This minimises loss of the first binding substance from the substrate. Covalent binding of an organic compound to a metal oxide is well known in the art, for example using the method described by Chu, C. W., et al. (J. Adhesion Sci. Technol., 7, pp.417–433, 1993) and Fadda, M. B. et al. (Biotechnology and Applied Biochemistry, 16, pp. 221–227, 1992).

According to a preferred embodiment the metal oxide membrane is comprised of aluminium oxide.

Such a membrane of aluminium oxide appears to have through-going channels that are hydrophilic in comparison to the surface of the membrane. Thus, advantageously, a hydrophilic liquid preferably enters the channels instead of spreading over the surface of the membrane. Therefore aluminium oxide membranes may accommodate for high densities of areas comprising different first binding substances. Aluminium oxide membranes having oriented through-going channels are disclosed by Rigby, W. R. et al. (Trans. Inst. Metal Finish., 68(3), p. 95, 1990) and are marketed by Anotec Separations Ltd., Oxon, UK. These membranes have been used to purify viruses, and to store enzymes for sensor purposes, but there is no suggestion with respect to their suitability as substrates for performing probe-based assays.

The present invention also relates to a method of manufacturing a device comprising membranes having oriented through-going channels according to the invention, wherein the first binding substance is synthesised in situ.

For example, using only a limited number of reagents, for a device comprising an oligonucleotide as the first binding substance usually four nucleotide compounds (dA, dT, dC, and dG for DNA, A, U, C, and G for RNA) and additional reagents such as blocking reagents, and protecting reagents, classical solid phase synthesis techniques can be used to provide a substrate with one or an array of a plurality of areas with oligonucleotide probes. Reagents can conveniently be applied to the through-going channels of a particular area using ink-jet technology. Ink-jet technology allows for the accurate deposition of defined volumes of liquid. In situ synthesis of oligonucleotide probes on a flat, non-porous substrate is well known in the art (see eg. T. P. Theriault: DNA diagnostic systems based on novel Chem-Jet technologies, IBC Conference on Biochip Array Technologies, Washington D.C., May 10, 1995).

According to a preferred embodiment, the nucleotide compounds are applied using electrostatic attraction. Electrostatic attraction diminishes the risk of splattering.

According to an alternative method of manufacturing a device comprising through-going channels according to the invention, the first binding substance is applied to the through-going channels of a particular area using ink-jet technology. This allows for purification of the first binding substance, and for example in case of an oligonucleotide probe for verification of its sequence, before application to the substrate.

For the reasons mentioned earlier, it is again preferred if the first binding substance is applied using electrostatic attraction.

The present invention also relates to the use of an electrochemically manufactured metal oxide membrane, preferably an aluminium oxide membrane, in the manufacture of any of the above described devices.

According to a preferred embodiment, a temperature difference is adjusted between different locations on the membrane during performance of the assay to create different hybridisation conditions at different membrane locations.

The use advantageously comprises a nucleic acid hybridisation assay or an immunological assay. In such an assay, a sample which comprises an analyte is brought into contact with a device according to the invention. The analyte is subsequently allowed to bind to the first binding substance which is attached to the substrate. Such binding is greatly facilitated by allowing the analyte to migrate through the porous substrate. Detection of binding can be performed by adding a second binding substance attached to a label, allowing said second binding substance to bind to the complex of first binding substance and analyte and determining whether the label is present at the position where the first binding substance was immobilised. Alternatively, the analyte may already have been provided with a label, in which case binding to the first binding substance can be detected directly, without the addition of a second binding substance.

The present invention also relates to a kit comprising any of the above mentioned devices which kit additionally comprises a detection means for determining whether binding has occurred between the first binding substance and the analyte. Preferably, such detection means may be a second binding substance provided with a label. Preferably, the label is capable of inducing a colour reaction and or capable of bio- or chemo- or photoluminescence.

The present invention also relates to a method for the detection of an analyte in a sample comprising the steps of
  a) contacting the sample with any of the above described devices,
  b) allowing binding to take place between the first binding substance and the analyte,
  c) detecting whether binding has occurred between first binding substance and analyte In this method the analyte may be a nucleic acid probe, an antibody, an antigen, a receptor, a hapten, and a ligand for a receptor.

The present invention will now be illustrated by the following examples.

EXAMPLE 1

Simultaneous detection of two different types of HIV-1 amplificate, a Wild Type RNA (WT) and a Calibrator RNA (Qa) using an aluminium oxide membrane in a flow through cell.

Analytes:

The WT-RNA and the Qa-RNA fragments represent a part from the GAG region of the HIV-1 genome. These fragments have equal lengths (145 nt) and identical sequences, apart from a 21 nt long region in the central part of the fragment. The sequences of the fragments are:

WT-RNA: 5'cccugcuaugucacuuccccuugguucucucaucuggccu ggugcaauaggcccugcaugc<u>acuggauacacucuaucccau</u>ucugca gcuuccucauugauggucucuuuuaacauuugcauggcugcuuga uguccccccacu3' (SEQID. NO.1)

Qa-RNA: 5'cccugcuaugucacuuccccuugguucucucaucuggccu ggugcaauaggcccugcaugc<u>gacugucaucuaucuacacugu</u>cugca gcuuccucauugauggucucuuuuaacauuugcauggcugcuugaug uccccccacu3' (SEQID. NO.2)

The sequence of the WT and Qa specific parts are underlined.

In this example two buffered solutions were used:

A phosphate buffer at pH 7.4 containing 8 g/l NaCl, ("incubation buffer").

A phosphate buffer at pH 7.4 containing 8 g/l NaCl and 0.05% Polysorbate (Tween 20), hereinafter denoted "wash buffer".

Substrate

Aluminium oxide membrane, thick 60 μpm, diameter 24 mm. Channels are 0.2 μm diameter, density is about 18 channels/μm² ("Anodisc 25", Whatman).

The membrane surface is coated with streptavidin by immersing the membrane in the incubation buffer contained 2 g/l streptavidin for 60 min. Subsequently, the membranes are washed using the wash buffer and air dried at room temperature.

Immobilisation of First Binding Substance

Two oligonucleotide probes, partially complementary to the WT- and QA fragments are applied:

WT-probe: 5'GAATGGGATAGAGTGCATCCAGTG3' (SEQID. NO. 3)

Qa-probe: 5'GACAGTGTAGATAGATGACAGTCG3' (SEQID. NO. 4)

both with a biotin molecule coupled to the 5' end.

Spots with a specific diameter are applied using a porous tip (nylon feeder) as found in the common "fineliner" writing pen (Hauser schreibtechnik GmbH, Gosheim Germany). Whereas the feeder tip spots the membrane, its other end is in fluid contact with a reservoir containing the probe solution (incubation buffer, probe concentration 25 μmol/L). Transfer of probe solution into the membrane is well controlled by the capillary interaction of membrane and feeder: the probe solution autonomously fills up those channels that are in physical contact with the feeder tip. In this example 2 lines with 3 spots of 0.5 mm diameter have been used (3 spots for each probe type). The distance between individual spots was 1 mm. After spotting and an incubation phase of 10 min. at room temperature, unbound probe material is washed away using the wash buffer. In this example, 4 identical substrates were produced in this way.

Hybridisation

Next, the membranes are introduced in a flow through cell and brought into contact with the incubation buffer containing the HIV RNA fragments.

Four sets of hybridisation conditions have been applied in 4 different experiments:

1 volume 25 μl containing $1.5*10^{12}$ molecules of QA RNA, no flow 2 volume 25 μl containing $1.5*10^{12}$ molecules of WT RNA, no flow 3 volume 25 μl containing $1.5*10^{12}$ molecules of QA RNA, continuous flow 4 volume 25 μl containing $1.5*10^{12}$ molecules of WT RNA, continuous flow With experiment 1 and 2 there is no transport of the buffer through the membrane. With experiment 3 and 4, the 25 μl RNA solution continuously flows through the membrane in two directions (back and forth) with a velocity of about 25 μl/min. To control this flow, an automated Hamilton dispenser was used. With all experiments hybridisation was at room temperature during 10 min.

Washing

After hybridisation the membranes are washed using 5 ml of the wash buffer.

Labelling and Detection

For detection, a probe that is generic for HIV RNA (SEQID #5) is allowed to interact with the membranes. This probe is contained in the incubation buffer (40 nmol/L). In each experiment a volume of 75 μl is used, without flow. The probes are labelled with the horseradish peroxidase (HRP) enzyme in a 1:1 ratio, using maleimide containing heterobifunctional cross-linkers (Hashida, S., et al.(1984) J.Applied Biochem.56, 56–63). Prior to the HRP coupling the probes were thiolated (Carlsson, J., et al. (1978) Biochem. J. 173, 723–737). After washing with 10 ml wash buffer, a solution containing 3,3',5,5'-tetramethylbenzidine hydrogenperoxide, TMB (Organon Teknika, art: 78510), is brought into contact with the membranes (no flow).

Result:

Interpretation of the results was with the unaided eye. In experiment 3 and 4, blue spots appear almost immediately at a location where a specific reaction is expected (spots containing WT probes turn blue using WT-RNA and spots containing Qa probes turn blue using Qa-RNA). With the spots containing probes that are not complementary to the RNA in the buffer no colouring was observed, although the area on the membrane in between the spots shows a slight bluish colour after several minutes, probably due to insufficient washing or some non specific binding. In experiment 1 and 2 a similar result is obtained, however, in these cases it takes about a minute before blue spots become visible.

In addition to the visual evaluation of the spots during the TMB reaction, the spots on the membranes in experiments 3 and 4 were evaluated using an imaging densitometer (Biorad GS700). To this end the membranes were removed from the flow-through cells (Table 1)

TABLE 1

| | Density of spots measured with densitometer | | |
|---|---|---|---|
| RNA analyte | spot with WT-probes [OD units] | spot with Qa-probes [OD units] | background area [OD units] |
| WT-RNA | 38 | 20 | 20 |
| Qa-RNA | 25 | 35 | 25 |

EXAMPLE 2

Oligonucleotide probes were covalently coupled to the Anopore membranes using 3-aminopropyl triethoxysilane (APS) as a linker between the alumina and the oligo. For the experiments Anodics 25 membranes with a diameter of 25 mm and a total surface area of 0.3 m² were used.

The membranes were activated by immersion in a nitric acid solution (0.4 mol/l) during 1 hour. After rinsing with water the membranes were dried and immersed in a 0.25% (v/v) solution of APS in water for 2 hours. Excess APS was removed by rinsing with water. After drying at 120° C. at reduced pressure the membranes were stored. Amino group concentration due to the coupling of the APS molecules was typical 2–3 umol/m².

Before coupling, the amino group terminated oligo nucleotides were activated by reaction with disuccinimidyl suberate (DSS, see eg. PIERCE BV, Immunotechnology Catalog & Handbook, 1990). The resulting succinimidyl group at the end of the oligo was used for coupling to the APS activated membrane. Labelling with $^{32}P$ was used for quantification of the results. Coupling with 500 ul oligo solution on an Anodisc membrane during 60 minutes resulted in a coupling yield of 1 $10^{-10}$ mol/$m^2$ oligo nucleotide.

EXAMPLE 3

Definition of an array pattern on an $Al_2O_3$ membrane using an ink-jet device. Using standard ink-jet technology small droplets having a diameter of 20–80 um can be generated and positioned on a substrate at high throughput rates at urn resolution. Using a commercially available desk-jet (HP 660C) in combination with the $Al_2O_3$ membranes arrays of a very high resolution have been obtained. Visual inspection with a microscope (magnification: 400×) shows perfectly round spots of aprox. 60 um diameter having very sharp margins. No signs of splattering, as is commonly observed when using non-porous surfaces was observed. We attribute the high array resolution to the high porosity of the material in combination with the hydrophilic character of the through-going channels.

EXAMPLE 4

Performing a sandwich immuno assay. Detection of human chorionic gonadotrophin (hCG) with an enzyme immuno assay using an aluminium oxide membrane as solid phase.

Coating of the Membrane

Small areas of aluminium oxide membranes (round with a diameter of 20 mm) were coated with a buffered solution (0.0127 mol/l phosphate and 0.140 mol/l NaCl at pH 7.4) containing 1 μg/ml monoclonal mouse antibody (OT-hCG4B) directed against hCG. The solution was applied by pipetting 10 μl droplets onto the membrane or by contact spotting using a polyester feeder (Hauser). After incubation at 37° C. for 30 minutes the membranes are ready for use.

Incubation

The positive samples were a mixture of 50 ul hCG with a concentration of 2000 IU/I and 50 ul mouse anti-hCG (OT-hCG-3A) conjugated with hors radish peroxidase (HRP) (1 ug/ml). This mixture was pre-incubated for 15 minutes. In the case of the negative control 50 ul buffer was mixed with 50 ul conjugate solution. Next the mixture (100 ul) was pipetted onto the membranes and incubated for 15 minutes at room temperature.

Washing and Detection

The membranes were extensively rinsed with a washing buffer (0.131 mol/l NaCl, 0.0127 mol/l phosphate and 0.5 ml/l Polysorbate 20) on a funnel. Finally the membranes were placed in a beaker containing a substrate for HRP based on 3,3',5,5'-tetramethylbenzydine and hydrogen peroxide (Organon Teknika). During 30 minutes incubation the results were observed visually and with a camera.

Results

Clear blue spots became visible within a few minutes where the membranes were coated with OT-hCG4B in the case of the positive samples. On the other parts of the membrane and with the negative control only a faint blue background colour could be observed after relative long incubation.

What is claimed is:

1. A method for the detection of an analyte in a sample the method comprising the steps of
   a) contacting the sample with a device comprising a substrate having through-going channels, the channels opening our on a surface for sample application, the channels in at least one area of the surface for sample application being provided with a binding substance capable of binding to an analyte, wherein the binding substance is within the through-going channels in the substrate;
   b) passing the sample back and forth through the membrane; and
   c) detecting whether binding has occurred between the binding substance and the analyte.

2. The method of claim 1, wherein the analyte comprises a nucleic acid, an antibody, an antigen, a receptor, a hapten or ligand for a receptor.

3. The method of claim 2, wherein the analyte is derivable from a human immunodeficiency virus.

4. The method of claim 1, wherein after step b) but before step c), the sample is again passed back and forth through the membrane in a manner sufficient to allow binding to take place between the binding substance and the analyte to be detected.

5. The method of claim 1, wherein the substrate is an electrochemically manufactured metal oxide membrane and the binding substance is covalently bound to the substrate.

6. The method of claim 5, wherein the metal oxide membrane is comprised of aluminum oxide.

7. The method of claim 1, wherein the substrate is an electrochemically manufactured metal oxide membrane and the binding substance is not covalently bound to the substrate.

8. The method of claim 7, wherein the metal oxide membrane is comprised of aluminum oxide.

9. The method of claim 1, wherein the binding substance is synthesized in situ.

10. The method of claim 9, wherein a compound for synthesizing the binding substance is applied to a particular area using ink-jet technology.

11. The method of claim 10, wherein the compound is applied using electrostatic attraction.

12. The method of claim 1, wherein the binding substance is applied to a particular area using ink-jet technology.

13. The method of claim 12, wherein the binding substance is applied using electrostatic attraction.

14. The method of claim 1, further comprising using the results of step to determine sequence information of a nucleic acid.

15. The method of claim 1, wherein the binding substance is an oligonucleotide.

16. The method of claim 1, wherein the binding substance is a sequence of amino acids.

17. The method of claim 1, wherein the binding substance is an antibody.

18. The method of claim 1, wherein the binding substance is an antigen.

19. The method of claim 1, wherein the binding substance is a receptor or a ligand for a receptor.

20. The method of claim 1, wherein the binding substance is a hapten.

* * * * *

UNITED STATES PATENT AND TRADEMARK OFFICE
CERTIFICATE OF CORRECTION

| | |
|---|---|
| PATENT NO. | : 6,864,102 B2 |
| APPLICATION NO. | : 09/845198 |
| DATED | : March 8, 2005 |
| INVENTOR(S) | : Hendrik Sibolt van Damme and Hermanus Johannes Maria Kreuwel |

It is certified that error appears in the above-identified patent and that said Letters Patent is hereby corrected as shown below:

Title page

Item (73), Assignee, "PamGene International B.V." should read --PamGene B.V.--.

Signed and Sealed this

Twenty-eighth Day of August, 2007

JON W. DUDAS
*Director of the United States Patent and Trademark Office*